United States Patent [19]
Cook

[11] Patent Number: 4,627,833
[45] Date of Patent: Dec. 9, 1986

[54] MICROSURGICAL SYSTEM CASSETTE ASSEMBLY

[75] Inventor: Kenneth P. Cook, Blue Bell, Pa.

[73] Assignee: Site Microsurgical Systems, Inc., Horsham, Pa.

[21] Appl. No.: 616,633

[22] Filed: Jun. 4, 1984

Related U.S. Application Data

[63] Continuation of Ser. No. 383,635, Jun. 1, 1982, Pat. No. 4,493,695.

[51] Int. Cl.$^4$ .............................................. A61M 1/00
[52] U.S. Cl. ....................................... 604/34; 604/317
[58] Field of Search ............... 433/91, 95; 128/200.14, 128/200.22; 604/22, 48, 246–250, DIG. 12, DIG. 13, 30–35

[56] References Cited

U.S. PATENT DOCUMENTS 4,303,376 12/1981 Siekmann ............................ 604/153
4,460,358 7/1984 Somerville ............................ 604/34

Primary Examiner—C. Fred Rosenbaum
Assistant Examiner—J. L. Kruter
Attorney, Agent, or Firm—Jason Lipow

[57] ABSTRACT

A cassette assembly for a microsurgical system. The cassette comprises a body portion, a collection vessel and a suction conduit which may be occluded to interrupt suction. The cassette may also include an occludable infusion conduit for providing infusion through the cassette to a surgical site.

11 Claims, 11 Drawing Figures

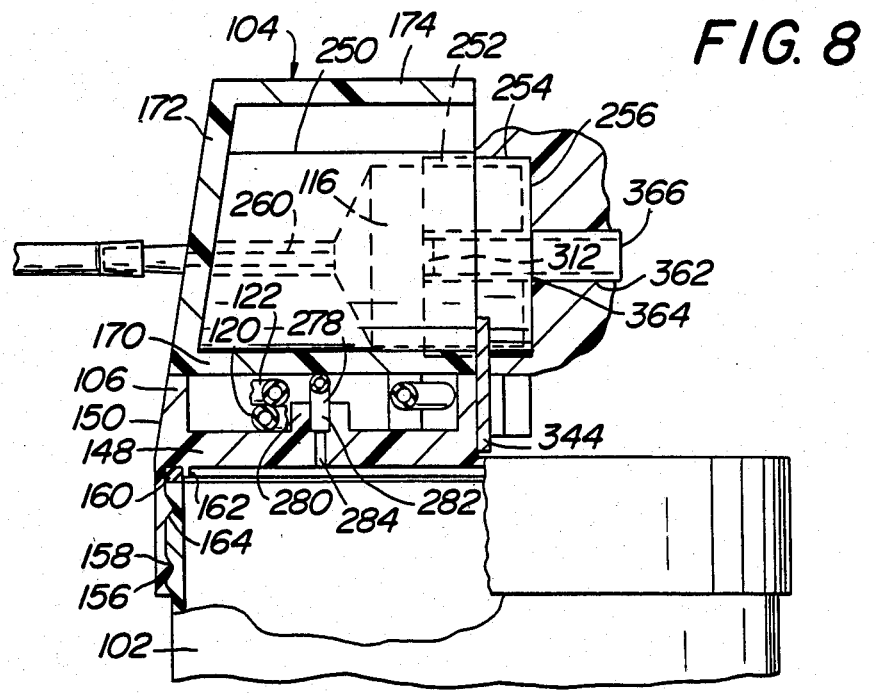
FIG. 8
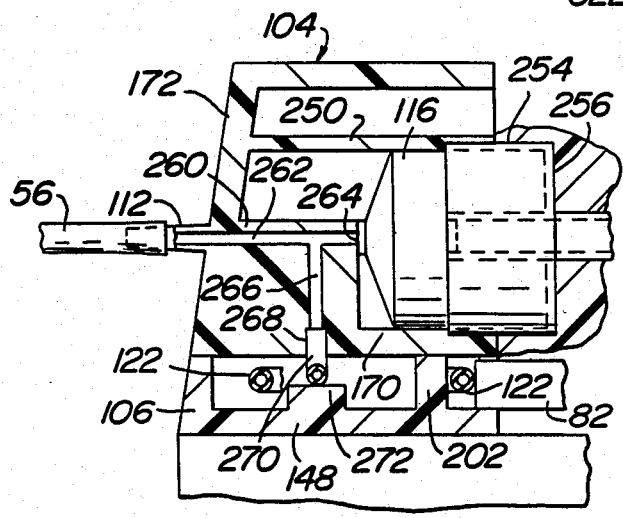
FIG. 9
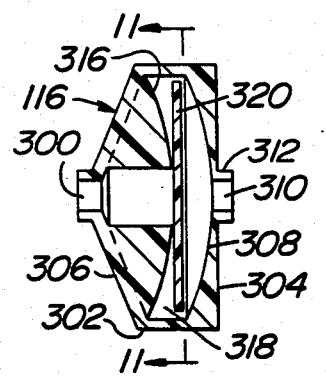
FIG. 11
FIG. 10

MICROSURGICAL SYSTEM CASSETTE ASSEMBLY

This is a continuation of application Ser. No. 383,635, filed June 1, 1982 now U.S. Pat. No. 4,493,695.

BACKGROUND OF THE INVENTION

This invention relates generally to surgical instruments, and more particularly, to microsurgical instruments.

Microsurgical systems are gaining ever-increasing acceptance in the surgical community for performing precise, minimum invasive surgery for various parts of the body. One particularly widespread microsurgical application is in the field of ophthalmology, and various manufacturers now produce opthalmic microsurgical systems. Examples of such systems are the Model 8000V system of Cavitron/Kelman and the Occutome II/Fragmatome II system of Cooper Medical Devices Corporation. Such systems have been used for performing anterior as well as posterior chamber surgery.

In either type of surgery, a remote handpiece having a small tool is used to either cut or mascerate the eye tissue while an irrigation or infusion liquid, such as Ringer solution, is brought to the situs of the surgery within the eye. The cut or mascerated tissue (detrius) is carried away from the surgical situs by a suction conduit or tube (which may or may not be connected to the tool) to some sort of collection vessel, e.g., a bag or bottle, located at the instrument or remote therefrom.

The suction produced in the suction conduit or line is usually controlled by the surgeon, via some switch means, e.g., a foot switch, so that the vacuum can be interrupted, when desired, during the surgery. In many applications it is also desireable to halt the flow of the infusion liquid upon the interruption of the suction line. The means for interrupting the infusion usually consists of an on/off valve or switch in the infusion line.

Heretofore, various prior art microsurgical systems have been arranged for receipt of portions of the suction line into a pinch valve in the instrument so that when the suction flow is to be stopped, the pinch valve occludes the line.

It will be appreciated by those skilled in the art that when the suction line is occluded, the inertia of the material within the line upstream of the occlusion point continues to produce suction at the entrance to the suction conduit. This residual vacuum can present substantial hazard in ophthalmic surgery applications, and particularly in anterior surgery applications since the anterior chamber is of much smaller volume than the posterior chamber. Thus, the residual or continued vacuum at the entrance to the suction line after the surgeon acts to interrupt the suction can result in the excessive evacuation of fluid from the anterior chamber or can result in the snagging and concomitant damage of delicate eye tissue.

In view of the foregoing and in the interest of surgical efficiency and patient safety, it is of considerable importance that there be precise control of the start-up and interruption of the vacuum in the suction line, while also insuring that upon the vacuum interruption, the suction line is neutralized to overcome any residual suction and inertial effects. In this regard, some microsurgical systems have incorporated venting means in the instrument itself to vent the suction line to the atmosphere when the suction line is occluded. Such systems also make use of replaceable hydrophobic filter means which is disposed in the instrument to prevent any material in the collection vessel from gaining ingress into the means which produce the vacuum, e.g., the vacuum pump.

While prior art microsurgical systems and techniques are generally suitable for their intended purposes, they leave much to be desired from the standpoint of simplicity of construction and use, and efficiency of operation. For example, with the prior art microsurgical systems described heretofore, it is necessary to connect the individual components making up the system, e.g., the filters, valves, collection bags or bottles, tubing, etc., to the instrument. Such preoperative setup procedures require substantial time, are complicated, messy and susceptible to error.

OBJECTS OF THE INVENTION

Accordingly, it is the general object of this invention to provide in a microsurgical system an integrated cassette assembly which overcomes the disadvantages of the prior art.

It is a further object of this invention to provide in a microsurgical system a cassette assembly which integrates various functions of prior art microsurgical systems into a simple, ready-to-use, effective unit.

It is a further object of this invention to provide in a microsurgical system a cassette assembly which can be readily connected to a microsurgical instrument to effect the immediate properative setup of suction and/or infusion conduits.

It is still a further object of this invention to provide for use in a microsurgical system an integrated cassette assembly incorporating a collector vessel, suction and infusion interrupter means, venting means and filter means.

It is still a further object of this invention to provide in a microsurgical system a disposable cassette assembly which is simple in construction and low in cost.

These and other objects of the instant invention are achieved by providing a cassette assembly for use in a microsurgical system comprising an instrument having control means, remotely connected means adapted to be disposed in the vicinity of the surgery situs and including an aperture, and first conduit means coupled to the aperture and arranged for carrying a fluid therethrough. The control means includes first means cooperating with the cassette assembly for selectively precluding the fluid from flowing through the first conduit. The cassette assembly is arranged for releasable securement to the instrument and comprises first port means for communication with the first conduit means, second port means through which the fluid flows and first occludable means coupled between the first and second port means. The first occludable means is arranged for cooperation with the first means when the cassette assembly is secured to the instrument to isolate the first and second ports from each other in response to a first signal, thereby precluding the fluid from flowing therethrough and through the first conduit means.

Other objects and many of the attendant advantages of this invention will be readily appreciated as the same becomes better understood by reference to the following detailed description when considered in connection with the accompanying drawing wherein:

DESCRIPTION OF THE DRAWING

FIG. 8 is a sectional view taken along line 8—8 of FIG. 4;

FIG. 9 is a sectional view taken along line 9—9 of FIG. 4;

FIG. 10 is a sectional view of a check valve forming a portion of the cassette assembly of the instant invention; and FIG. 11 is a sectional view taken along line 11—11 of FIG. 10.

DETAILED DESCRIPTION OF THE PREFERRED EMBODIMENT

Figures 1, 2:
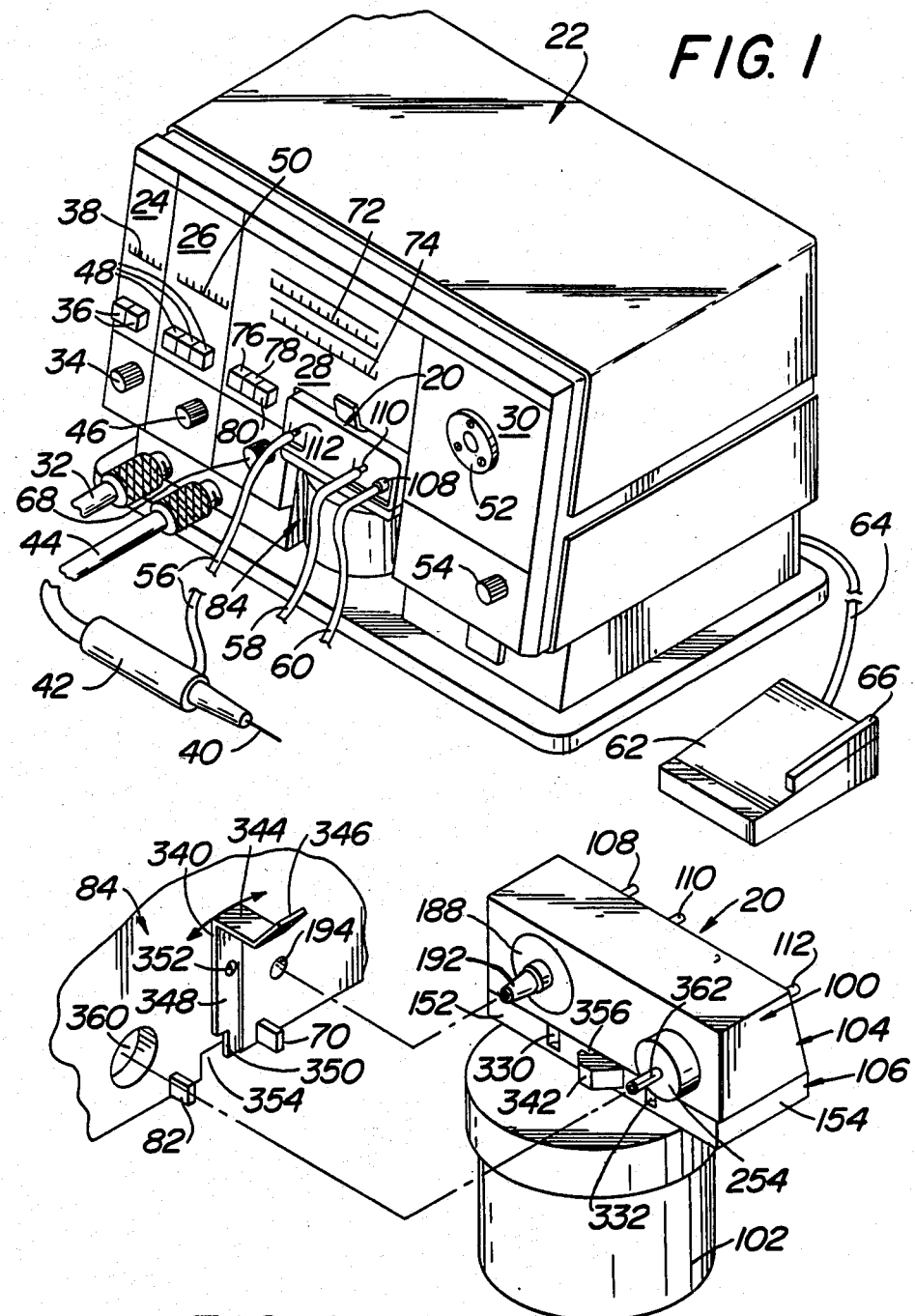
FIG. 1 is a perspective view of a microsurgical system including the cassette assembly of the instant invention.
FIG. 2 is an enlarged, exploded perspective view of a portion of the microsurgical system and the cassette assembly shown in FIG. 1.

Referring now to various figures of the drawing wherein like reference characters refer to like parts, there is shown generally at 20 in FIG. 1 a cassette assembly for use in a microsurgical system. The system shown in FIG. 1 is a complete microsurgical system suitable for a wide variety of ophthalmic surgical applications. To that end, the complete system 20 basically comprises an instrument 22 having a console including plural modular units, such as an ultrasonic (fragmentation) unit 24, a cutting unit 26, an infusion/aspiration or I/A unit 28 and a fiber optic unit 30.

The basic building block of the system consists of the I/A unit 28. This unit is arranged for performing extracapsular cataract procedures as well as other surgical procedures. If anterior segment surgery is required, the cutting unit 26 is added to the console. The addition of the fiber optic unit renders the system suitable for both pars plana and anterior segment intraocular microsurgery. Finally, if lens emulsification or aspiration is desired, the ultrasonic unit 24 is added to the console.

The cassette assembly 20 of the instant invention is arranged for use with the I/A unit 28 of the instrument. Thus, the details and features of the ultrasonic unit 24, the cutting unit 26 and the fiber optic unit 30 will not be described herein. Suffice to say that the ultrasonic unit 24 is arranged to operate and drive a remote hand-held ultrasonic (fragmentation) tool (not shown), via a connecting cable 32. The amount of ultrasonic energy provided to the tool is established by the setting of a rotary adjustment knob 34 on the unit's front panel. A pair of on/off switches 36 and LED display 38 are also provided on the unit's front panel. The LED display provides an indication of the ultrasonic energy provided to the tool.

The cutting unit 26 is arranged to drive a tool 40 mounted in a handpiece 42, via a communicating cable 44. The tool 40 can be of any suitable types, such as a reciprocating cutter, a rotary cutter, a guillotine cutter, a scissors, etc. The speed of the cutting action is established by the setting of a rotary knob 46 on the cutting unit's front panel. On/off and other switches 48 are also provided on the front panel. The front panel also includes a LED display 50 for indicating operating speed.

The fiber optic illumination unit 30 provides variable, cool white, illumination for intraocular procedures and for intraocular photography. To that end, unit 30 comprises a light source (not shown) located within the unit for producing the white light. The light is provided, via a fiber optic cable (not shown), to the surgical situs. The cable is connected by a connector coupling 52 on the front panel of the illumination unit 30. The intensity of illumination provided by the unit 30 is established by the setting of a rotary adjustment knob 54 on the front panel of the unit 30.

The I/A unit 28 controls the removal of the cut or mascerated tissue produced by the operation of the cutting tool 40 or by the ultrasonic tool (not shown), while also controlling infusion of liquid into the surgery situs. In particular, unit 28 produces a vacuum in a suction conduit or tube 56 which is connected between the cassette assembly 20 and the cutting tool handpiece 42 or some other means, e.g., a needle (not shown), arranged to be located at the surgery situs. An infusion liquid, such as a Ringer solution, is provided to the surgery situs, via a conduit or tube 58 connected between the cassette assembly 20 and the handpiece 42 or some other means, e.g., a needle, located at the surgery situs. The infusion liquid is supplied to the cassette assembly from a supply bottle (not shown), via a conduit 60. As will be described in detail later, the I/A unit 28 includes means which cooperates with means in the cassette assembly to enable or disable the suction and/or the infusion under control of the surgeon.

During surgery the cutting action of the tool 40 mascerates or cuts the tissue at the operating situs. The mascerated tissue and the liquid infused into the operating situs, via line 58, is carried by the suction line 56 away from the situs to the cassette assembly for collection in its collection bottle. The vacuum in the suction line is produced by a pump (not shown) in the I/A unit and is coupled, via means in the cassette assembly, to the suction line 56, as will be described later. The degree of vacuum in the suction line can be varied linearly by the surgeon by the depression of foot switch 62 connected by a cable 64 to the instrument 22.

Accordingly, when the foot switch 62 is depressed fully, the amount of vacuum produced in the I/A suction line is at the value as established by the setting of an adjustable control knob 68 on the unit's front panel. When the foot switch 62 is released partially, the amount of vacuum in the suction line is a portion of the maximum as established by the setting of knob 68. When the foot switch is fully released, the I/A unit immediately interrupts the vacuum in the suction line by the operation of its suction interrupter bar 70 (FIG. 2) closing the suction path in the cassette assembly 20.

The foot switch 62 also includes a button 66 for controlling the operation of the cutting unit 26. A pair of LED displays 72 and 74 are provided on the I/A unit's front panel to indicate preset and existing vacuum conditions.

As stated earlier, the I/A unit is also arranged to control the flow of infusion liquid through the cassette assembly 20 from the liquid source to the surgical situs. To that end, three push-button knobs 76, 78 and 80 are provided on the front panel of the I/A unit. Button 76 is the "off" button and, when depressed, causes an infusion interruptor bar 82 (FIG. 2) in the I/A unit to close the infusion liquid flow path in the cassette assembly to stop the flow of liquid to the surgery situs. Button 78 is the "on" button and, when depressed, holds the interruptor bar 82 in a position so that the infusion path in the cassette is open to allow the flow of infusion liquid to the surgery situs. The push-button 80 is the "automatic" button and, when depressed, gives control of the operation of the interruptor bar 82 over to the foot switch 62. Accordingly, when the I/A unit is in the automatic mode, release of the foot switch by the surgeon causes the interruptor bar 82 to operate to interrupt the flow of infusion liquid to the surgery situs.

The I/A unit includes a large cove or receiver 84 for receipt and mounting of the cassette assembly 20. The cassette assembly includes means which cooperates with means in the receiver for releasably mounting the assembly in the I/A receiver.

Figure 3:
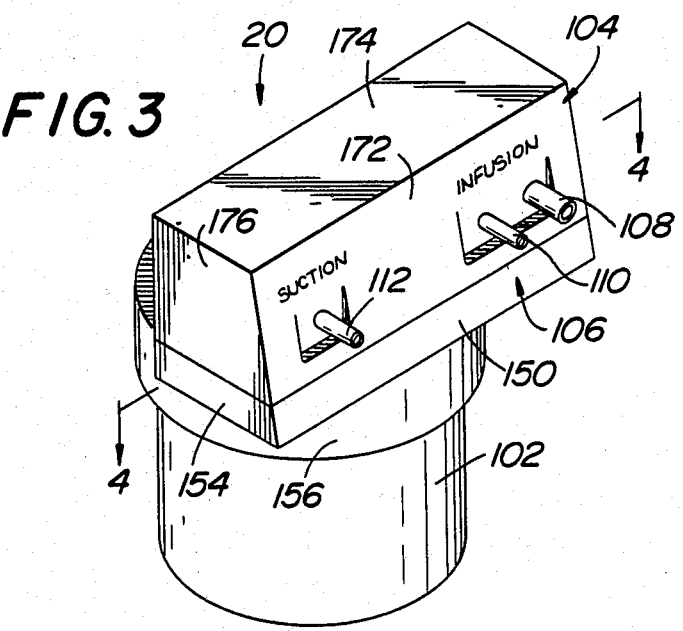
FIG. 3 is an enlarged perspective view of the cassette assembly shown in FIGS. 1 and 2.

Turning now to FIGS. 2–11, the details of the cassette assembly 20 will be described. Basically the cassette assembly comprises a body or housing 100, and a collector bottle 102 depending therefrom. The housing includes various components, to be described later, and is made up of a pair of mating, molded plastic sections, namely, an upper section 104 and a lower section 106. As can be seen in FIG. 3, the upper section 104 includes an infusion liquid input port 108, in the form of a female luer to which the conduit 60 is secured, an infusion liquid output port 110, in the form of a male luer to which the conduit 58 is secured, and a suction port 112, in the form of a male luer to which the suction conduit 56 is secured.

A hydrophobic filter 114 (FIG. 5) is mounted within the upper section of the housing and is arranged when the cassette assembly 22 is located within the I/A unit's receiver 84 to communicate with the vacuum producing pump (not shown) in the unit. The filter 114 is a conventional device, such as a Millex-FG filter made by Millipore. Filter 114 is arranged to prevent any liquid from entering into the pump, while also precluding any bacteria in the I/A unit from gaining ingress into the cassette assembly.

A one-way check valve 116 (see FIG. 8) is also mounted within the upper section 104 of the cassette assembly housing. The check valve is arranged to communicate with an electronic vent valve (not shown) within the I/A unit when the cassette is mounted within the unit's receiver. The electronic valve is of conventional construction and allows the suction line to vent to the atmosphere, upon the interruption of the vacuum. This action neutralizes the vacuum in the suction line, thereby obviating any residual vacuum effects which could occur by the inertia of the liquid in the line at the moment the vacuum is interrupted. The check valve 116 permits the venting to occur through the electronic valve while precluding any liquid or material in the suction line from entering into that valve.

Figure 4:
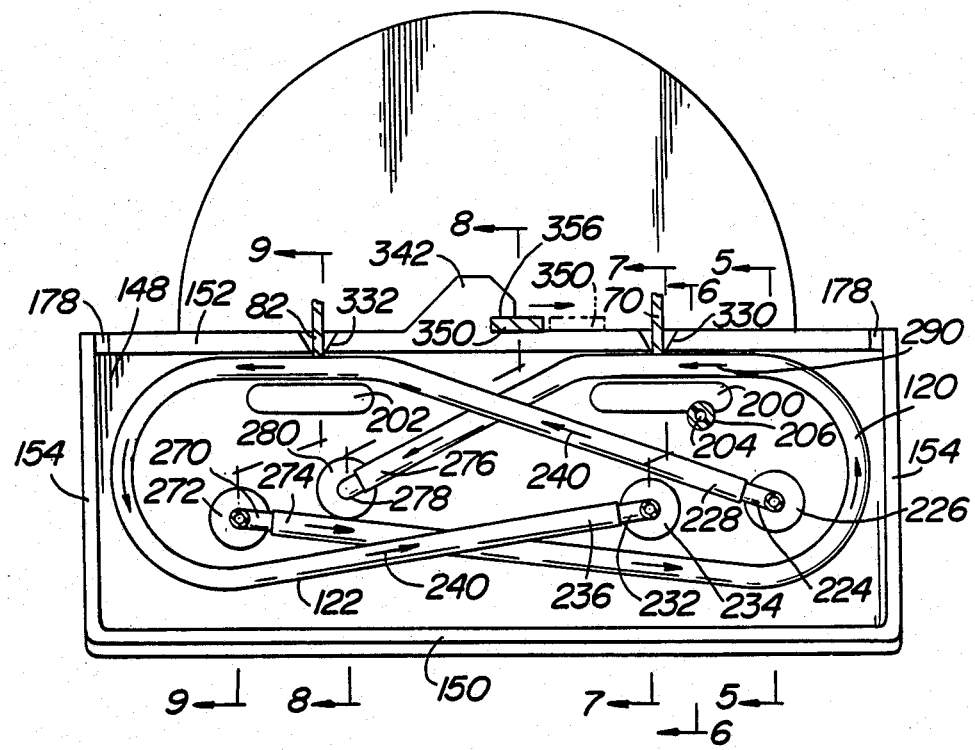
FIG. 4 is an enlarged sectional view taken along line 4—4 of FIG. 3.

As stated earlier, the cassette assemby 20 includes passageway means for the suction line and the infusion line which are acted upon interruptor bars 70 and 82, respectively, to interrupt the fluid flows therethrough, under the control of the I/A unit. Such passageway means comprise a pair of occludable conduit sections 120 and 122 mounted in the lower section of the housing, as shown in FIG. 4. Each conduit section consists of a length of flexible tubing which is arranged to be engaged by an associated interrupter bar to squeeze (occlude) the passageway through the section.

The suction conduit section 120 is connected in series in the path of the suction line between the port 112 and the collection bottle 102. The collection bottle is in turn connected in the suction path between the filter 114 and the suction conduit section 120. The check valve 116 is connected to the junction of the suction port 112 and the suction conduit section 120 to enable the venting of the suction line downstream of the collection bottle upon the interruption of the suction by the I/A unit's interruptor bar 70.

The infusion conduit section 122 is connected between infusion output port 110 and the infusion input port 108.

As shown clearly in FIGS. 4–9, the lower section 106 of the housing basically comprises a bottom wall 148 of generally rectangular shape having a front wall 150, a rear wall 152 and a pair of sidewalls 154 projecting upward about the periphery thereof. A circular cap portion 156 is disposed contiguous with the bottom wall and basically comprises a circular sidewall including internal helical threads 158. A rubber gasket in the form of a ring 160 is located at the inside interface of the sidewall 156 and the top of the cap (FIG. 8). A downward projecting annular flange 162 holds the gasket ring in place. The periphery of the collection bottle 102 includes helical threads 164 disposed thereabout to mate with the threads 158 on the cap to enable the bottle to be screwed into place in the cap.

The upper section 104 of the housing includes a planar bottom wall 170, a front wall 172, a top wall 174 and a pair of sidewalls 176. A pair of ribs (not shown) project downward from the outer surface of the bottom wall 170 along each of the sidewalls 176 for receipt within respective slots 178 (FIG. 4) in the top edge of the back wall 152 of the lower section 106. When the sections are secured together, the sidewalls 154 and 176 of the top and bottom section are flush with each other, as are the front wall portions 150 and 172 of the top and bottom sections, respectively.

Figure 5:
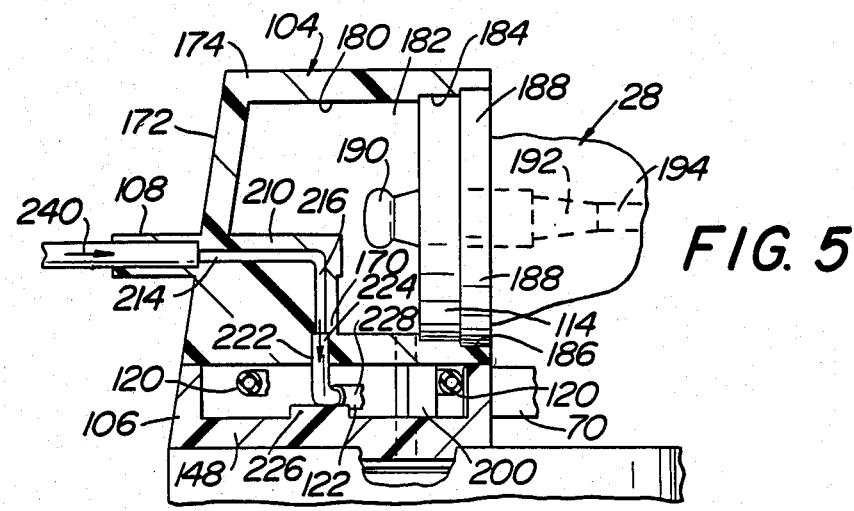
FIG. 5 is a sectional view taken along line 5—5 of FIG. 4.
Figure 6:
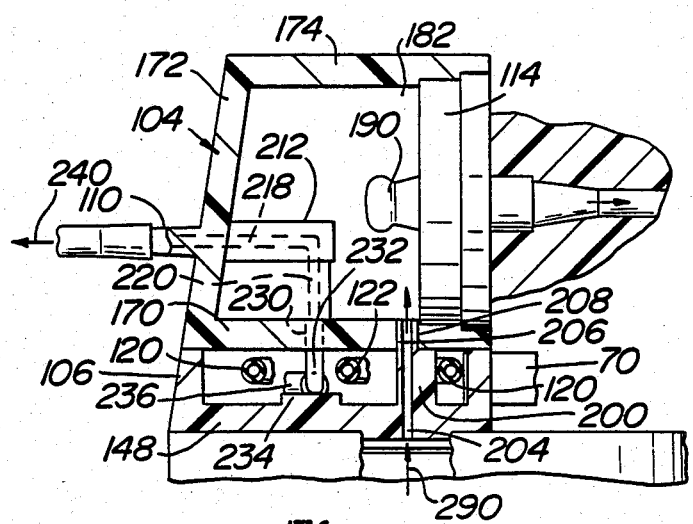
FIG. 6 is a sectional view taken along line 6—6 of FIG. 4.
Figure 7:
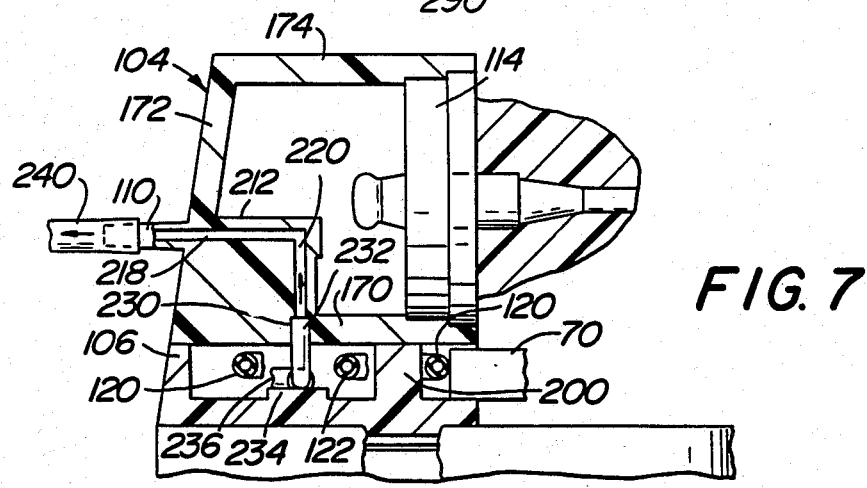
FIG. 7 is a sectional view taken along line 7—7 of FIG. 4.

Referring now to FIGS. 5–7, it can be seen that in the interior of the upper section 104 there is a circular sidewall 180 forming a cylindrical cavity 182. The mouth of the cavity includes an annular ledge 184 adapted to receive the filter 114. As can be seen, the filter 114 includes a disk-like portion which is disposed on ledge 184. The sidewall 180 also includes a second annular ledge 186 contiguous with the back of the top wall 174 and bottom wall 170. The filter 114 also includes an entrance port 190 in the form of a female luer, which is in open communication with the interior of chamber 182 and an outlet port 192, in the form of a male luer adapted to be received within a passage 194 in the I/A unit's receiver 84. The passageway 194 communicates with the electronic vent valve in the I/A unit. A ring-like wafer 188 is mounted on the ledge 186, with the outlet luer 192 extending therethrough, to hold the filter in place in the chamber or cavity 182.

As can be seen in FIG. 4, a pair of elongated stops 200 and 202 project upward from the bottom wall 148 of the lower section 106. The stops cooperate with the interruptor bars to squeeze or occlude the suction and infusion conduit sections therebetween upon operation of the interrupter bars, as will be described later.

As can be seen in FIG. 6, a suction aperture 204 extends through the bottom wall 150 of the bottom section and terminates in a tubular chimney section 206 projecting upward from the backstop 200. The upper portion of the chimney section 206 extends into an opening 208 in the bottom wall 170 of the top section. Thus, the suction aperture 204 provides fluid communication between the interior of the collection bottle 102 and the interior of the filter chamber 182.

As can be seen in FIGS. 5-7, disposed within the interior of the chamber 182 are a pair of wall sections 210 and 212 (FIGS. 5 and 6). Wall section 210 projects inward from the top section's front wall 172, upward from its bottom wall 170 and in alignment with the infusion input luer 108. In a similar manner, the wall section 212 projects inward from the top section's front wall 104, upward from its bottom wall 170 and in alignment with the infusion output luer 110. The wall section 210 includes a horizontal passageway portion 214 and a communicating vertical passageway portion 216. Passageway portion 214 is in communication with the interior of luer 108. In a similar manner, the wall section 212 includes a horizontal passageway portion 218 and a vertical passageway portion 220. The horizontal passageway portion 218 is in communication with the interior of the male luer 110. The lower end of passageway section 216 is in the form of an enlarged mouth 222 for receipt of the upwardly extending leg of a tubular, L-shaped connector 224. The connector rests on a circular ledge or pad 226 projecting upward from the top surface of the bottom wall 148 of the lower housing section. The other end of the L-shaped connector 224 is disposed within one end 228 of the infusion conduit section 122.

In a similar manner, the lower end of passageway 220 is in the form of an enlarged mouth 230. The mouth 230 receives the upper section of an L-shaped, tubular connector 232. The other end of connector 232 is located within the end 236 of the infusion conduit section 122. Connector 232 rests on a circular ledge or pad 234 projecting upward from the top surface of the bottom wall 148 of the lower section 106.

As will be appreciated from the foregoing, infusion liquid in enabled to flow through the cassette assembly in the direction of the arrows denoted by the reference numerals 240 in FIGS. 4, 5 and 7 as follows: into luer 108, through passageway sections 214, and 216, through L-shaped connector 224, through infusion conduit section 122, through L-shaped connector 232, through passageways 220 and 218 to outlet luer 110.

A second circular sidewall 250 is located within the interior of the upper housing section 104 as shown in FIG. 8. The sidewall 250 is arranged to form a chamber to receive the check valve 116. At the mouth of the sidewall 250 is an annular ledge 252 adapted to receive the sidewall 254 of a bucket-shaped cap 256. The cap 256 holds the check valve in place within the circular sidewall 250.

A wall section 260 projects inward from the top section's front wall 172, upward from its bottom wall 170 and aligned with the suction luer 112. The wall section 260 includes a horizontal passageway 262 in communication with the interior of the luer 112 at one end thereof and terminating in an opening 264 at the back edge of the wall section 260. The opening 264 is arranged to communicate with the check valve 116 to allow venting of the suction line, as will be described later. A vertical passageway 266 communicates with the horizontal passageway 262 in the wall section 260. The lower end of passageway 266 includes an enlarged bore 268 adapted to receive the upper end of an L-shaped conduit connector 270. The other end of the connector 270 is disposed within one end of 274 of the suction conduit section 120. The connector 270 rests upon a circular ledge or pad 272 projecting upward from the bottom wall 148 of the lower section. The other end 276 of the suction conduit section 120 receives one end of an L-shaped, tubular connector 278. The other end of connector 278 is received within a bore 282 in a circular ledge or pad 280 projecting upward from the bottom wall 148 of the lower section. The bore 282 is in communication with a suction aperture passageway 284 extending through the bottom wall 148 and into communication with the interior of the collection bottle 102.

The flow of material through the suction path in the cassette assembly 20 is shown by the arrows denoted with the reference numeral 290 in FIGS. 4 and 6 and is as follows: from the conduit 56 to luer 112, through passageways 262 and 266, through L-shaped connector 270, through suction conduit section 120, through L-shaped connector 278, through aperture 284, into bottle 102. The remainder of the suction path from the bottle to the vacuum pump in the I/A unit consists of aperture 290, chamber 182, filter 114 and passageway 192.

The check valve includes an outlet opening 300 (FIG. 10) which communicates with the passageway 262, via the opening 264 at the end of the wall section 260. The check valve 116 is shown clearly in FIGS. 10 and 11. Basically the check valve 116 comprises a hollow body having a circular sidewall 302, a planar back wall 304 and a conical front wall 306. The interior surface of the back wall 304 is concave at 308. The back wall 304 includes a central opening 310 formed by a flanged annular lip 312. A plurality of generally V-shaped splines 314 (FIG. 11) projects inward from the inner surface of the conical front wall 306. The top surface 316 of the splines is convex. The opening 300 extends through the center of the splines into the interior of the check valve. The interior of the check valve is a chamber denoted by the reference numeral 318. A diaphragm 320 is located within the chamber 318 and basically comprises a resilient material disk loosely located within the chamber 318.

As can be seen in FIG. 11, the space between legs of adjacent V-shaped splines is denoted by the reference numeral 322 and is in communication with the outlet 300. Moreover, the diameter of the diaphragm 320 is slightly less than the length of the convex surface of the splines measured in the diametric direction. Thus, fluid, e.g., air, can flow through outlet 300, the communicating spaces 322, around the periphery of the diaphragm 320 to opening 310 and from thence through the open electronic valve within the I/A unit to allow the venting of suction line 56 to the atmosphere through the open electronic valve when desired. Should any liquid attempt to pass through the valve, such as could occur due to the momentum imparted to the liquid at the time that the suction is interrupted, such liquid impacts the diaphragm 320 causing it to close the opening 310 in the check valve, thereby preventing any liquid from gaining ingress into the open electronic valve.

The means for interrupting the vacuum in the suction line and a means for interrupting the flow of infusion line consists of the heretofore mentioned interrupter bars 70 and 82, respectively. As also mentioned heretofore, each of those bars is arranged to engage an associated portion of the conduit section to close or occlude the conduit section, thereby interrupting the flow therethrough. In order to provide access for the interrupter bars to the associated conduit section, the back wall 152 of the lower housing section includes a pair of openings 330 and 332. Each opening is larger at its entrance than at its exit. The opening 330 is disposed opposite to the stop 200. The opening 332 is disposed opposite to the stop 202. The interrupter bar 70 is arranged to be reciprocated through the opening 330 into the interior of the lower section to engage the suction conduit section 120 disposed contiguous with that opening to squeeze or occlude that portion of the conduit section against the stop 200. This action immediately interrupts suction in suction line 56. As noted heretofore, when the interrupter bar 70 is operated to interrupt the suction, the electronic valve and the I/A unit opens, whereupon the suction line 56 is vented to the atmosphere, via the check valve and associated electronic vent valve. The check valve, operates as noted heretofore, to prevent any egress of material into the electronic vent valve.

The infusion interrupter bar 82 operates in a similar manner to the suction interrupter bar 70. To that end, the infusion interrupter bar is extended through opening 332 to engage the infusion conduit section between it and the stop 202, thereby squeezing the infusion conduit section 122 shut and thus, interrupting the flow of infusion liquid to the infusion output conduit 58.

The extension of the infusion interruptor bar 82 can be accomplished either in response to the depression of the "close" button 76 on the front panel of the I/A unit or can be under control of the foot switch 62 when the I/A unit is in the "automatic" mode as established by the depression of the push-button 80. When the push-button 78 of the I/A unit is depressed, the unit is in the "open" state with the interruptor bar retracted so long as the "open" button 78 is depressed.

The means for releasably mounting the cassette assembly in the I/A unit's receiver 84 comprises a pivoting latch 340 mounted on the front wall of the receiver. The latch 340 is adapted to engage a catch 342 projecting from the back wall 152 of the cassette assembly 20. As can be seen in FIG. 2, the latch 340 basically comprises a planar body portion 348, and a projecting portion 344 terminating in an angularly extending free end 346. The free end 350 of the body portion 348 is notched. The latch 340 is mounted on the receiver wall by a screw 352 to enable the latch to be pivoted about the screw. The receiver 84 includes a recess 354 immediately adjacent the notched end 350 of the latch 340. The recess 354 is adapted to accommodate the catch 342 of the cassette assembly. That catch is in the form of a projection including a slot 356 extending parallel to the surface of back wall 152. The slot 356 is arranged to receive the notched free end 350 of the pivoting latch to lock the cassette assembly in place. To that end, the latch is pivoted in the counter-clockwise direction from that shown in FIG. 2 to move the free end of the latch away from the recess 354 in the receiver. The cassette is then inserted into the receiver so that its catch 342 is received within the recess 354 and with the free ends of the interrupter bars entering the associated slots in the rear of the cassette assembly body. The latch 344 is then pivoted in the clockwise direction until the notched end 350 of the latch is located within the slot 356, thereby locking the cassette in place.

In order to accommodate the cup-shaped bucket 254 projecting from the back of the cassette assembly, the front wall of the receiver 84 of the I/A unit also includes a circular recess 360 for receipt of the bucket therein. In the center of the recess is the passageway (not shown) which communicates with the electronic vent valve.

A sleeve 362 extends through the central opening 364 in the back wall of the bucket member of the cassette assembly and receives the flanged lip 312 of the check valve to provide a passage to the interior of the check valve. The free end of the sleeve 362 is rounded at 366. This sleeve is adapted to fit into the passageway in the I/A unit's recess 360 to provide access to the electronic vent valve therein (not shown).

As will be appreciated from the foregoing, the cassette assembly of the instant invention is an integrated unit which simplifies preoperative setup by eliminating all the messy wires, pinch valves and confusion heretofore synonymous with microsurgical preoperative setups. In this regard, the single disposable cassette of the instant invention plugs into the receiver of the instrument's I/A unit to serve all modular functions of the unit. Thus, there is no need to inventory an expensive variety of components. Moreover, the cassette assembly offers the choice of either gravity-fed or automatically controlled infusion, while operating in conjunction with the I/A unit to prevent the occurrence of residual suction upon the interruption of vacuum. Moreover, the interruption of suction or infusion can be established independently of the other. Thus, for instance, the cassette can be used to start and stop infusion to a surgical situs without the use of any suction operation.

It must be pointed out at this juncture that while the invention has been specifically described herein with reference to ophthalmic surgery, it is clear that it can be used for any type of microsurgery or "non-invasive" surgery.

Without further elaboration, the foregoing will so fully illustrate my invention that others may, by applying current or future knowledge, readily adapt the same for use under various conditions of service.

I claim:

1. A cassette assembly adapted for releasable securement to a control console for use in ophthalmic surgery comprising:

a housing having at least one rigid surface and having an externally accessible suction port;

a first port internal to said housing in fluid communication with said suction port;

a second port internal to said housing and means through which fluid may flow to a source of vacuum in a control console;

a first occludable tubular conduit means disposed in said housing and coupled between said first and second ports and providing fluid communication therebetween;

at least a portion of said occludable tubular conduit means aligned with said housing rigid surface;

a collection vessel supported by said housing and having a first port for providing fluid communication between a source of vacuum and said collection vessel and having a second port in fluid communication with said first occludable tubular conduit means.

2. The cassette of claim 1 wherein said occludable tubular conduit means includes a piece a flexible rubber tubular conduit having an occludable portion disposed along said rigid surface of said housing.

3. The apparatus of claim 2 wherein said housing includes an upper portion and a lower portion;

wherein said occludable tubular conduit means is disposed in said lower portion and said lower portion includes an opening therein to expose an occludable portion of said occludable tubular conduit means.

4. The cassette assembly of claim 2 wherein said housing includes a body portion and a collection vessel removably mounted on said body portion.

5. A cassette assembly adapted for releasable securement to a control console for use in ophthalmic surgery comprising:
  a housing;
  an externally accessible fluid access port means on said housing for providing fluid communication between a surgical situs and the housing;
  a first port in fluid communication with said fluid access port means disposed interior to said housing;
  a second port means interior to said housing and through which fluid may flow;
  a flexible first occludable tubular conduit means coupled between said first and second interior port means and providing fluid communication therebetween, a portion of said first occludable tubular conduit means facing a backstop means;
  backstop means aligned with at least a portion of said first occludable tubular conduit means to provide a support against which said first occludable tubular conduit means may be compressed to shut off fluid communication between said first and second interior ports when cooperating with an interrupting occluding means on a control console;
  a collection vessel supported by said housing and having a first port for providing fluid communication between a source of vacuum and said collection vessel and having a second port in fluid communication with said first occludable tubular conduit means.

6. The cassette assembly of claim 5 further including a check valve in fluid communication with said fluid access port means and said first port.

7. A cassette assembly adapted for releasable securement to a control console for use in ophthalmic surgery comprising:
  a housing;
  an externally accessible fluid access port means on said housing for providing fluid communication between a surgical situs and the housing;
  a first port in fluid communication with said fluid access port means disposed interior to said housing;
  a second port means interior to said housing and through which fluid may flow;
  a flexible first occludable tubular conduit means coupled between said first and second interior port means and providing fluid communication therebetween, a portion of said first occludable tubular conduit means facing a backstop means;
  backstop means aligned with at least a portion of said first occludable tubular conduit means to provide a support against which said first occludable tubular conduit means may be compressed to shut off fluid communication between said first and second interior ports when cooperating with an interrupting occluding means on a control console;
  said housing including a body portion and a collection vessel removably mounted to said body portion.

8. The cassette assembly of claim 7 further including a vent providing fluid communication to said collection vessel through said housing.

9. The cassette assembly of claim 7 further including a filter disposed in said vent passage.

10. A cassette assembly adapted for releasable securement to a control console for use in ophthalmic surgery comprising:
  a housing having an externally accessible suction port;
  a first port internal to said housing and in fluid communication with said suction port;
  a second port internal to said housing and means through which fluid may flow to a source of vacuum in a control console;
  a piece of flexible rubber tubular conduit disposed in said housing and coupled between said first and second ports and providing fluid communication therebetween, said flexible rubber tubular conduit having an occludable portion disposed along a rigid surface of said housing against which said flexible rubber tubular conduit may be compressed to shut off fluid communication between said first and second ports when cooperating with an interrupting occluding means on a control console;
  said housing including an upper portion and a lower portion;
  wherein said flexible rubber tubular conduit is disposed in said lower portion and said lower portion includes an opening therein to expose an occludable portion of said flexible rubber tubular conduit in response to a signal; and,
  a selectably occludable vent means in fluid communication with said first port and adapted for venting said first port to the atmosphere in response to a signal;
  said vent means disposed in said upper housing portion, containing said suction port.

11. A cassette assembly adapted for releasable securement to a control console for use in ophthalmic surgery comprising:
  a housing;
  an externally accessible fluid access port on said housing for providing fluid communication between a surgical situs and the housing;
  a first port in fluid communication with said fluid access port means disposed interior to said housing;
  a second port means interior to said housing and through which fluid may flow;
  a flexible first occludable tubular conduit means coupled between said first and second interior port means and providing fluid communication therebetween, a portion of said first occludable tubular conduit means facing a backstop means;
  backstop means aligned with said portion of said first occludable tubular conduit means to provide a support against which said first occludable tubular conduit means may be compressed to shut off fluid communication between said first and second interior ports when cooperating with an interrrupting occluding means on a control console;
  a check valve in fluid communication with said fluid access port means and said first port; and,
  said housing including a body portion and a collection vessel removably mounted to said body portion.

* * * * *